(12) United States Patent
Lou et al.

(10) Patent No.: US 11,540,984 B2
(45) Date of Patent: Jan. 3, 2023

(54) NANOEMULSIONS AND A METHOD FOR MAKING THE SAME

(71) Applicant: Conopco, Inc., Englewood Cliffs, NJ (US)

(72) Inventors: Anjing Lou, Seymour, CT (US); Congling Quan, Woodbridge, CT (US); Teanoosh Moaddel, Watertown, CT (US); Maria Buchalova, Sandy Hook, CT (US)

(*) Notice: Subject to any disclaimer, the term of this patent is extended or adjusted under 35 U.S.C. 154(b) by 0 days.

(21) Appl. No.: 17/056,583

(22) PCT Filed: May 14, 2019

(86) PCT No.: PCT/EP2019/062300
§ 371 (c)(1),
(2) Date: Nov. 18, 2020

(87) PCT Pub. No.: WO2019/224048
PCT Pub. Date: Nov. 28, 2019

(65) Prior Publication Data
US 2021/0205186 A1 Jul. 8, 2021

(30) Foreign Application Priority Data
May 23, 2018 (EP) .................................... 18173916

(51) Int. Cl.
| | | |
|---|---|---|
| *A61K 8/06* | (2006.01) | |
| *A61K 8/44* | (2006.01) | |
| *A61K 8/67* | (2006.01) | |
| *A61Q 19/00* | (2006.01) | |
| *A61K 8/49* | (2006.01) | |

(52) U.S. Cl.
CPC .............. *A61K 8/068* (2013.01); *A61K 8/064* (2013.01); *A61K 8/447* (2013.01); *A61K 8/492* (2013.01); *A61K 8/675* (2013.01); *A61K 8/676* (2013.01); *A61Q 19/00* (2013.01); *A61K 2800/21* (2013.01); *A61K 2800/52* (2013.01)

(58) Field of Classification Search
None
See application file for complete search history.

(56) References Cited

U.S. PATENT DOCUMENTS

| | | |
|---|---|---|
| 3,274,063 A | 9/1966 | Nieper |
| 3,786,076 A | 1/1974 | Morelle |
| 3,819,825 A | 6/1974 | Goodwin |
| 4,201,235 A | 5/1980 | Ciavatta |
| 4,707,354 A | 11/1987 | Garlen et al. |
| 4,826,828 A | 2/1989 | Wilmott et al. |
| 4,885,157 A | 5/1989 | Fiaschetti |
| 5,133,958 A | 7/1992 | Stuckler |
| 5,198,465 A | 3/1993 | Dioguardi |
| 5,254,331 A | 10/1993 | Mausner |
| 5,326,484 A | 7/1994 | Nakashima et al. |
| 5,416,075 A | 5/1995 | Carson |
| 5,472,706 A | 5/1995 | Friedman |
| 5,582,817 A | 10/1996 | Otsu |
| 5,667,768 A | 9/1997 | Ramin |
| 5,887,747 A | 3/1999 | Burklin et al. |
| 5,899,177 A | 5/1999 | Binversie et al. |
| 6,013,279 A | 11/2000 | Klett-Loch |
| 6,149,925 A | 11/2000 | Mammone |
| 6,602,492 B2 | 5/2003 | Iwasaki |
| 6,592,908 B1 | 7/2003 | Crum |
| 6,858,217 B2 | 2/2005 | Kerschner |
| 6,869,598 B2 | 3/2005 | Unilever |
| 6,863,897 B2 | 8/2005 | Love et al. |
| 6,992,062 B2 | 1/2006 | Usala |
| 7,008,638 B2 | 7/2006 | Huglin et al. |
| 7,105,570 B2 | 12/2006 | Iwasaki |
| 7,300,649 B2 | 11/2007 | Tanojo |
| 7,381,423 B2 | 3/2008 | Huglin et al. |
| 7,740,831 B2 | 6/2010 | Chiba |
| 8,119,111 B2 | 2/2012 | Malek |
| 8,241,681 B2 | 8/2012 | Herrmann |
| 8,299,127 B2 | 10/2012 | Anjing et al. |
| 8,357,649 B2 | 1/2013 | Chieffi |
| 8,361,446 B2 | 1/2013 | Muller |
| 8,425,882 B2 | 4/2013 | Lou et al. |
| 8,431,620 B2 | 4/2013 | Del Gaudio et al. |
| 8,388,985 B2 | 5/2013 | Leser et al. |
| 8,440,172 B2 | 5/2013 | Johncock |
| 8,513,311 B2 | 8/2013 | Sagalowicz et al. |
| 8,795,643 B1 | 8/2014 | Anthony |
| 8,815,800 B2 | 8/2014 | Pashkovski |
| 8,865,143 B2 | 10/2014 | Lu |

(Continued)

FOREIGN PATENT DOCUMENTS

| | | |
|---|---|---|
| BR | PI0905347 | 7/2013 |
| CA | 2337772 | 1/2000 |

(Continued)

OTHER PUBLICATIONS

Search Report and Written Opinion in EP16169468; dated Oct. 14, 2016.
L-Cystine; Sigma-Aldrich Product Information C8755.
Tareen; The Effects of Short Term Adminstration of a Novel Glutathione Precursor (FT061452) RTRN Research Hub 2012 pp. 1-2; 2012; 1-2.
Tareen; The Effects of a Glutathione Precursor FT061452 on Serum and Intracellular Glutathione Levels; ClinicalTrials.gov The Effects of a Glutathione Precursor FT061452 on Serum 2013; 2013 United States of America.

(Continued)

*Primary Examiner* — Kyung S Chang
(74) *Attorney, Agent, or Firm* — Edward A. Squillante, Jr.

(57) ABSTRACT

Nanoemulsions and a method for making the same are described. The nanoemulsions comprise a skin benefit agent in the water phase and they are made from two macroemulsions that have non-identical pH values.

16 Claims, No Drawings

(56) References Cited

U.S. PATENT DOCUMENTS

| | | |
|---|---|---|
| 2002/0106390 A1 | 8/2002 | Huglin et al. |
| 2003/0194417 A1 | 10/2003 | Iwasaki |
| 2005/0192229 A1 | 1/2005 | Perricone |
| 2005/0191330 A1 | 9/2005 | Huglin et al. |
| 2005/0271726 A1 | 12/2005 | Crum |
| 2006/0063718 A1 | 3/2006 | Perricone |
| 2006/0257351 A1 | 11/2006 | Chiba |
| 2007/0213234 A1 | 9/2007 | Yaghmur et al. |
| 2007/0253986 A1 | 11/2007 | Stange et al. |
| 2008/0255247 A1 | 10/2008 | Sagalowicz et al. |
| 2008/0311058 A1 | 12/2008 | Lou et al. |
| 2008/0311211 A1 | 12/2008 | Leser et al. |
| 2009/0087464 A1 | 4/2009 | Hedges |
| 2009/0118380 A1 | 5/2009 | Del Gaudio et al. |
| 2009/0131543 A1 | 5/2009 | Weitz et al. |
| 2009/0263513 A1 | 10/2009 | Marini |
| 2010/0119560 A1 | 5/2010 | Kim et al. |
| 2010/0161029 A1 | 6/2010 | Filippini et al. |
| 2010/0305169 A1 | 12/2010 | Robinson |
| 2010/0305218 A1 | 12/2010 | Wooster et al. |
| 2010/0322876 A1 | 12/2010 | Nguyen |
| 2011/0165311 A1 | 7/2011 | Bruijn de et al. |
| 2011/0183040 A1 | 7/2011 | Ermolin |
| 2011/0189298 A1 | 8/2011 | Vos et al. |
| 2012/0034183 A1 | 2/2012 | Cohen |
| 2012/0177708 A1 | 7/2012 | Leser et al. |
| 2013/0209527 A1 | 8/2013 | Del Gaudio et al. |
| 2013/0209529 A1 | 8/2013 | Kumar et al. |
| 2014/0375562 A1 | 12/2014 | Pereira |
| 2016/0000669 A1 | 1/2016 | Hinman et al. |
| 2016/0120794 A1 | 5/2016 | Liu et al. |
| 2016/0215238 A1 | 7/2016 | Vetter et al. |
| 2017/0319443 A1 | 11/2017 | Weitz et al. |
| 2020/0009034 A1* | 1/2020 | Damodaran ......... A61K 8/4926 |

FOREIGN PATENT DOCUMENTS

| | | |
|---|---|---|
| CN | 101214199 | 7/2008 |
| CN | 101401775 | 4/2009 |
| CN | 101530377 | 9/2009 |
| CN | 101721930 | 6/2010 |
| CN | 201799243 | 4/2011 |
| CN | 102150866 | 8/2011 |
| CN | 102755847 | 10/2012 |
| CN | 104874305 | 9/2015 |
| CN | 105148758 | 12/2015 |
| CN | 105919827 | 7/2016 |
| CN | 109276515 | 1/2019 |
| CN | 109199878 | 9/2019 |
| EP | 0815040 | 10/1996 |
| EP | 1269978 | 1/2003 |
| EP | 2572701 | 3/2013 |
| EP | 2921160 | 9/2015 |
| FR | 2608424 | 6/1988 |
| FR | 2660196 | 10/1991 |
| FR | 2997852 | 5/2014 |
| GB | 720561 | 12/1954 |
| GB | 874368 | 8/1961 |
| GB | 987800 | 3/1965 |
| GB | 1050756 | 12/1966 |
| GB | 1235667 | 6/1971 |
| GB | 2212722 | 8/1989 |
| JP | 61227515 | 10/1986 |
| JP | 4099716 | 3/1992 |
| JP | 5032533 | 2/1993 |
| JP | 2009242321 | 10/2009 |
| JP | 2010280675 | 12/2010 |
| JP | 2014196275 | 10/2014 |
| JP | 2015030689 | 2/2015 |
| JP | 201656111 | 4/2016 |
| KR | 20050028669 | 3/2005 |
| KR | 20060025365 | 3/2006 |
| KR | 101002433 | 12/2010 |
| KR | 20160123753 | 10/2016 |
| WO | WO9505852 | 3/1995 |
| WO | WO0003689 | 1/2000 |
| WO | WO0128502 | 4/2001 |
| WO | WO03039724 | 5/2003 |
| WO | WO03080011 | 10/2003 |
| WO | WO03105806 | 12/2003 |
| WO | WO2005110370 | 11/2005 |
| WO | WO2009101272 | 10/2009 |
| WO | WO2012094638 | 7/2012 |
| WO | WO2013044111 | 3/2013 |
| WO | WO2014131871 | 9/2014 |
| WO | WO2015066777 | 5/2015 |
| WO | WO2015152420 | 10/2015 |
| WO | WO-2018113636 A1 * | 6/2018 ............ A61K 8/347 |

OTHER PUBLICATIONS

Tyrrell; Correlation Between Endogenous Glutathione Content and Sensitivity of CulturedHuman Skin Cells; Photochemistry and Photobiology 1988 vol. 47 No. 3 pp. 405-412; 1988; p. 405-412; vol. 47, No. 3; United States of America.

Dolphin; Glutathione: Chemical, biochemical and medical aspects; Cell Biochemistry & Function Apr. 1990 vol. 8 Issue 2 pp. 139; Apr. 1990; 139; vol. 8, Iss 2; United States of America.

Meister; Glutathione Metabolism and Its Selective Modification; The Journal of Biological Chemistry ; 1988; pp. 17205-17208; vol. 263 No. 33; United States of America.

Meister; Selective Modification of Glutathione Metabolism; Science 200; 1985; pp. 471-477; 220.

Search Report in EP17156112; dated Apr. 7, 2017.

Search Report and Written Opinion in EP17180848; dated Oct. 6, 2017.

Search Report and Written Opinion in PCTEP2017083207; dated Mar. 19, 2018.

Kumano et al.; Studies of water-in-oil (w/o) emulsion stabilized with amino acids or their salts; Journal Society Cosmetic Chemists; 1977; pp. 285-314; XP001058465; vol. 28, No. 5.

Hydrating Mask; Mintel Database GNPD; Aug. 1, 2014; XP002778756; pp. 1-3.

Mela BB Cream Pact IRF 35 SPF 50+/PA+++,; Mintel Database GNPD, Record ID 2740667; 2014; XP002778757; pp. 1-5; Korea (South).

Search Report and Written Opinion in PCTEP2018066640.

Yang et al.; Night-use and day-use nanoemulsions as passive targeted transdermal drug delivery system for whitening skin and inhibiting pigmentation, and their preparation methods; Database CA (Online); Jan. 1, 2009; abstract; XP2773779.

Yang et al.; Daily use type, night use type and auxiliary type nanometer emulsion for external use for expelling spot on skin, and manufacture method thereof; Database CA (Online); Jan. 1, 2009; abstract only ; XP2773778.

Search Report and Written Opinion in EP18173916; dated Oct. 23, 2018; European Patent Office (EPO).

Search and Written Opinion in PCTEP2019062300; dated Jul. 12, 2019.

IPRP2 for PCTEP2018066640; dated Sep. 27, 2019.

Search Report and Written Opinion in EP19166593; dated Sep. 24, 2019.

makingcosmetics.com; Making Cosmetics (makingcosmetics.com) Ceteareth-20; 2021; 3.

IPRP2 in PCTEP2019062300; dated May 11, 2020.

\* cited by examiner

NANOEMULSIONS AND A METHOD FOR MAKING THE SAME

FIELD OF THE INVENTION

The present invention is directed to a nanoemulsion and a method for making and using the same. More particularly, the invention is directed to a nanoemulsion that is oil continuous and possesses, in its aqueous phase, a high concentration of benefit agent that is not soluble in water at 25° C. and at neutral pH.

BACKGROUND OF THE INVENTION

Nanoemulsions are becoming increasingly popular for use in personal care compositions. They are stable and have a high surface area in view of their unit volume. Nanoemulsions can carry actives in their water and oil phases and are desirable since they enhance penetration of active through the skin as well as topical benefits delivered to consumers that employ end use compositions formulated with the same.

Personal care compositions that are nanoemulsions or made to include nanoemulsions as additives must be formulated at a pH that does not irritate the skin of consumers. Such a pH is typically close to neutral, and unfortunately, the pH that makes dissolution of certain skin benefit agents very difficult in the water phase of the nanoemulsion.

It is of increasing interest to deliver nanoemulsions that not only are skin tolerant but that also possess high concentrations of certain benefit agents, especially in the water phase.

This invention, therefore, is directed to a nanoemulsion and a method for making and using the same. The nanoemulsion, surprisingly, has a high concentration of benefit agent in its water phase and is delivered at a pH that is very pleasant for topical application to skin. The method for making such a nanoemulsion can surprisingly be achieved by passing macroemulsion through a low energy shearing process.

ADDITIONAL INFORMATION

Efforts have been disclosed for making nanoemulsions. In U.S. Published Patent Application No. 2017/0112764A1, nanoemulsions having reversible continuous and dispersed phases are described.

Even other efforts have been disclosed for making nanoemulsions. In Chinese Published Patent Application CN104874305A, a method for preparing nanoemulsions is described.

Still other efforts have been disclosed for making nanoemulsions. In WO 15066777A1, nanoemulsions having fatty alcohols are described.

None of the additional information above describes a nanoemulsion and method for making a nanoemulsion as set forth in the present claims.

SUMMARY OF THE INVENTION

In a first aspect, the present invention is directed to a method for making an oil continuous nanoemulsion comprising the steps of:
(a) combining, in no particular order, a first and a second oil continuous macroemulsion, the first macroemulsion having a pH from 10 to 14 and skin benefit agent in its water phase and the second macroemulsion having a pH from 2 to 5;
(b) mixing the first and second macroemulsions to produce a mixture of macroemulsions, the mixture having macroemulsions with both a pH from 10 to 14 and a pH from 2 to 5; and
(c) shearing the mixture of macroemulsions to produce a nanoemulsion having a particle size from 150 to 900 nm, the nanoemulsion comprising 0.15 to 5% by weight skin benefit agent in its water phase.

In a second aspect, the present invention is directed to the nanoemulsion made in the first aspect of this invention.

In a third aspect, the present invention is directed to the use of the nanoemulsion of the second aspect of the invention to deliver a skin benefit.

In a fourth aspect, the present invention is directed to an end use composition comprising the nanoemulsion of the first aspect of this invention.

In a fifth aspect, the present invention is directed to a macroemulsion having a pH from 10 to 14 and comprising a water insoluble skin benefit agent in its aqueous phase.

All other aspects of the present invention will more readily become apparent from the description and examples which follow.

Skin, as used herein, is meant to include skin on the arms (including underarms), face, feet, neck, chest, hands, legs, buttocks and scalp (including hair). Particle size, as it relates to the macro- and nanoemulsions, means the volume average diameter of the water droplets in microns or nanometers. Water droplet size may be measured with a commercially available Malvern Mastersizer. End use composition (water or oil continuous but preferably oil continuous) is a composition for topical application and includes a cream, lotion, balm, serum, gel, mousse, aerosol, deodorant, antiperspirant, shampoo, conditioner, make-up or personal wash, including bars and liquids. Such an end use composition can be the nanoemulsion of this invention or nanoemulsion added to an end use composition to formulate the same or to boost the same at the time of use by a consumer. Skin benefit agent, as herein defined, is a water insoluble component that delivers a benefit to skin after being topically applied. Water insoluble means having a solubility in water of no more than 0.05% by weight, and preferably, no more than 0.03% by weight, and most preferably, no more than 0.015% by weight at 25° C., atmospheric pressure and neutral pH. In the invention, water insoluble material or agent is forced to have a solubility in water of 0.15 to 5%, and preferably, 0.15 to 5% by weight at 25° C., atmospheric pressure and neutral pH. Neutral pH as used herein means having a pH from 5.5 to 7.5. In a preferred embodiment, the end use composition is oil continuous as is the nanoemulsion of this invention that is suitable to be added thereto.

In another preferred embodiment, the end use composition of this invention is a leave-on skin lotion, cream or liquid personal wash composition. Unless specified, emulsion as generally used means the macro- and nanoemulsion as described herein. In the absence of explicitly stating otherwise, all ranges described herein are meant to include all ranges subsumed therein. The term comprising is meant to encompass the terms consisting essentially of and consisting of. For the avoidance of doubt, a nanoemulsion of this invention comprising oil, water, and skin benefit agent is meant to include a nanoemulsion consisting essentially of the same and a nanoemulsion consisting of the same. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE INVENTION

As to the oil continuous macroemulsions used to prepare the nanoemulsions of the present invention, the same typically comprise from 30 to 70%, and preferably, from 35 to 65%, and most preferably, from 40 to 60% by weight water, based on total weight of the macroemulsion and including all ranges subsumed therein.

Within the macroemulsion, oil typically makes up from 25 to 65%, and preferably, 35 to 60%, and most preferably, 40 to 55% by weight oil, based on total weight of the macroemulsion and including all ranges subsumed therein. Such macroemulsions typically have a particle (water droplet) size from 1 to 30, and preferably, from 2 to 25, and most preferably, from 3 to 20 microns, including all ranges subsumed therein.

The oil suitable for use in this invention (i.e., for macroemulsion and nanoemulsion) is limited only to the extent that same is a liquid at room temperature and suitable for use in a topical composition.

Illustrative examples of the oils suitable for use include silicone oils.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Nonvolatile silicone oils useful in this invention include polyalkyl siloxanes, polyalkylaryl siloxanes and polyether siloxane copolymers. Such essentially non-volatile polyalkyl siloxanes useful herein include, for example, polydimethylsiloxanes (like dimethicone) with viscosities of from 5 to 100,000 centistokes at 25° C.

An often preferred silicone source is a cyclopentasiloxane and dimethicone solution.

Suitable esters for use to make emulsion in this invention include:

(1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;

(2) Ether-esters such as fatty acid esters of ethoxylated fatty alcohols;

(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 mono stearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Sterol esters, of which soya sterol and cholesterol fatty acid esters are examples thereof.

Still other oils that may be used in this invention include triglycerides (animal and/or vegetable) like soybean oil, sunflower oil, coconut oil, palm kernel oil, castor oil, rapeseed oil, palm oil, grape seed oil, caprylic/capric triglyceride, safflower oil, fish oil or mixtures thereof.

Even other oils suitable for use include mineral oil, jojoba oil, isoparaffins, $C_{12}$-$C_{15}$ alkyl benzoates, polyalphaolefins, isohexadecane, petrolatum, mixtures thereof (including with those oils above) or the like. Soybean and sunflower oil are often preferred triglyceride oils.

Caprylic capric triglyceride is another often preferred oil for use in the emulsions of the present invention.

Adjusters suitable to modify the pH of macroemulsion aqueous phases (and resulting nanoemulsion aqueous phases) of this invention may be used. Such pH adjusters include triethylamine, NaOH, KOH, $H_2SO_4$, HCl, $C_6H_8O_7$ (i.e., citric acid) or mixtures thereof. The pH adjusters are added at amounts such that the high pH macroemulsion has a pH from 10 to 14, and preferably, from 11 to 13, and most preferably, from 11 to 12.5, and the low pH macroemulsion has a pH from 2 to 5, and preferably, from 2 to 4, and most preferably, from 2 to 3.5.

The water phase pH of the desired macroemulsions of the present invention is assessed by using conventional instrumentation such as a pH meter made commercially available from Thermo Scientific®. Thus, nanoemulsions made from the shearing of the macroemulsions will preferably have an aqueous phase pH from 5.5 to 7.5, a direct result of the nanoemulsion mixing ratios.

The emulsifiers suitable for use in this invention typically have an HLB from 2.5 to 7.5, and preferably, from 3 to 6.5, and most preferably, from 3 to 6, including all ranges subsumed therein.

Illustrative examples of the types of emulsifiers that are suitable for use in this invention are propylene glycol isostearate, glycol stearate sorbitan sesquioleate, lecithin, oleth-2, steareth-2, ceteth-2 glyceryl stearate, PEG-30 dipolyhydroxystearate.

Still other emulsifiers suitable for use include glycol distearate, glyceryl oleate, sorbitan monooleate, sorbitan tristearate, sorbitan trioleate, sorbitan monopalmitate, lauryl PEG-10, (trimethylsiloxy)silylethyl dimethicone (Dow Corning® ES-5300) or mixtures thereof.

Emulsifiers typically make up from 2.5 to 10, and preferably, from 3.5 to 8, and most preferably, from 4.5 to 7.5% by weight of the emulsion (i.e., macro- and nanoemulsion) including all ranges subsumed therein.

As to the skin benefit agent suitable for use in this invention, the same is limited only to the extent that it is capable of being topically applied to skin, water insoluble as herein defined, and suitable to dissolve in water when the water pH is adjusted to 10 to 14.

Illustrative examples of the benefit agents suitable for use in this invention include acids, like amino acids, such as phenylalanine, tyrosine, tryptophan, cysteine or a mixture thereof.

Typically, the amount of skin benefit agent used in the macroemulsion having a pH from 10 to 14 is from 0.3 to 10%, and preferably, from 0.5 to 8%, and most preferably, from 1 to 6% by weight, based on total weight of the macroemulsion and including all ranges subsumed therein. Therefore, the amount of skin benefit agent in the water phase of the nanoemulsions of the present invention is from 0.15 to 5%, and preferably, 0.25 to 4%, and most preferably, from 0.5 to 3.5% by weight, based on total weight of the nanoemulsion and including all ranges subsumed therein. In a most preferred embodiment, the skin benefit agent used is cysteine.

It is also within the scope of the present invention to optionally include an oil soluble active in the oil phase of the macro- and nanoemulsions. The only limitation with respect to such oil soluble active is that the same is suitable to provide a benefit to skin when topically applied.

Illustrative examples of the types of oil soluble actives that may optionally be used in this invention include vitamins like Vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble actives suitable for use include resorcinols like 4-ethyl resorcinol, 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an especially preferred embodiment, the optional oil soluble active used in this invention is a retinoic acid precursor.

Preferably the retinoic acid precursor is retinol, retinal, retinyl propionate, retinyl palmitate, retinyl acetate or a mixture thereof. Retinyl propionate, retinyl palmitate and mixtures thereof are typically preferred.

Still another retinoic acid precursor suitable for use is hydroxyanasatil retinoate made commercially available under the name Retextra® as supplied by Molecular Design International. The same may be used in a mixture with the oil soluble actives described herein.

When the optional (i.e., 0.0% by weight) oil soluble active is used in the oil phase of the emulsions of this invention, it typically makes up from 0.001 to 8%, and preferably, from 0.05 to 4.5%, and most preferably, from 0.1 to 3% by weight of the emulsion, based on total weight of the emulsion and including all ranges subsumed therein.

Preservatives can desirably be incorporated into the emulsions (and end use compositions) of this invention to protect against the growth of potentially harmful microorganisms, although it is within the scope of the invention for the such emulsions to be preservative free. Suitable traditional preservatives for use in this invention are alkyl esters of para-hydroxybenzoic acid. Other preservatives include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the total weight of the emulsion or end use composition, including all ranges subsumed therein. Combinations of 1,2-octanediol and phenoxyethanol, or iodopropynyl butyl carbamate and phenoxyethanol are preferred, with phenoxyethanol and 1,2-octanediol, collectively and preferably, making up less than 1.8% by weight of the total weight of the emulsion or end use composition of the present invention. Also preferred is a preservative system with hydroxyacetophenone alone or in a mixture with other preservatives.

Thickening agents are suitable for use in the emulsions of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, sclerotium, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers are yet another class of effective thickening agent. This category includes crosslinked polyacrylates such as the Carbomers, polyacrylamides such as Sepigel 305 and taurate copolymers such as Simulgel EG and Aristoflex AVC, the copolymers being identified by respective INCI nomenclature as Sodium Acrylate/Sodium Acryloyldimethyl Taurate and Acryloyl DimethyltaurateNinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

Amounts of the thickening agent, when used, may range from 0.001 to 22%, and preferably, from 0.1 to 17%, and most preferably, from 0.2 to 16% by weight of the emulsion, based on total weight of the emulsion and including all ranges subsumed therein. Maltodextrin, xanthan gum, and carboxymethyl cellulose are the often preferred.

Fragrances, fixatives and exfoliants may optionally be included in emulsions of the present invention. Each of these substances may range from about 0.05 to about 5%, preferably between 0.1 and 3% by weight.

Conventional humectants may optionally be employed as additives in the emulsions of the present invention to assist in moisturizing skin when such emulsions are topically applied. These are generally polyhydric alcohol type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 10 to 15% by weight of the total weight of macro- and nanoemulsion emulsion.

The emulsions of the present invention may optionally include water soluble actives like Vitamin $B_2$, Vitamin $B_3$ (niacinamide), Vitamin $B_6$, Vitamin C, mixtures thereof or the like. Water soluble derivatives of the vitamins may also be employed. For instance, Vitamin C derivatives such as ascorbyl tetraisopalmitate, magnesium ascorbyl phosphate and ascorbyl glycoside may be used. Other water soluble actives suitable for use in the water phase of the emulsions include extracts like sage, aloe vera, green tea, grapeseed, thyme, chamomile, liquorice or rosemary extract or mixtures thereof. Water soluble sunscreens like ensulizole may also be used. Total amount of water soluble actives (including mixtures) when present in the emulsions of the present invention may range from 0.0 to 15%, preferably from 0.001 to 10%, optimally from 0.01 to 4% by weight, based on total weight of the emulsion and including all ranges subsumed therein.

When making the macroemulsions of the present invention, the desired ingredients may be mixed to produce water and oil phases. The same may be mixed under moderate shear with emulsifier under atmospheric conditions with temperature being from ambient to 85° C. Mixing to make macroemulsion can be done with a magnetic stir bar or may be accomplished in a commercially available mixer equipped with, for example, an impeller (e.g., turbine or anchor), or a rotor/stator high shear mixer made commercially available by suppliers like Esco-Labs, AG, Silverson® or Charles Ross & Son. Mixing to typically shear rate can vary and is preferable set such that the resulting emulsions are not aerated to the point of displaying visual air pockets. Often, mixing to make macroemulsion is set with a stirrer or scraper at 35 to 500, and preferably, at 40 to 250, and most preferably, at 45 to 150 rpm. Shearing with a rotor/stator to make nanoemulsion is typically accomplished with rotation being set from 1000 to 8000, and preferable, from 2000 to 7000, and most preferably, from 2500 to 6,250 rpm, including all ranges subsumed therein.

The resulting macroemulsions typically have a viscosity from 750 to 55,000 cps, and preferably, from 2,000 to 40,000 cps, and most preferably, from 5,000 to 30,000 cps, including all ranges subsumed therein, where the viscosity of the macroemulsions is measured with a Brookfield (DV-1+) Viscometer, temperature 25° C. and set at 20 RPM, RV6 for 30 seconds.

The resulting macroemulsions may be fed after premixing or simultaneously to a high shear mixer (like a rotor/stator) mixer or a homogenizer in order to produce the desired nanoemulsions of the present invention. Such nanoemulsions preferably have a particle droplet size from 150 to 900 nm, and preferably, from 250 to 825 nm, and most preferably from 250 to 800 nm, including all ranges subsumed therein. Nanoemulsion production is surprisingly achieved after one pass through a homogenizer, (when a homogenizer is selected) with pressure set from 50 to 2000, and preferably, from 250 to 1000, and most preferably, from 300 to 800 psi, including all ranges subsumed therein. Preferred devices for making the nanoemulsions of the present invention are the Silverson® rotor/stator mixer or homogenizer (such as a Sonic Sonolator). In an especially preferred embodiment, and when a homogenizer is used, pressure is set from 50 to 1000 psi. The viscosity of the resulting nanoemulsions will fall within the ranges identified for the macroemulsions, and especially since they are a mixture of the same.

Typically, when making the nanoemulsion of the present invention, from 50 to 90, and preferably, from 55 to 75, and most preferably, from 60 to 75% by weight of high pH macroemulsion is used, based on total weight of the macroemulsion combination of high plus low pH macroemulsion used to make the nanoemulsion, including all ranges subsumed therein. In a preferred embodiment, the weight percent ratio of high to low pH macroemulsions used in such that the resulting nanoemulsion will have a pH from 5.5 to 7.5. In an especially preferred embodiment, from 50 to 60% by weight high pH macroemulsion is used in the emulsion combination and the pH of the resulting nanoemulsion is from 5.5 to 6.5. In another especially preferred embodiment, from 70 to 80% by weight high pH macroemulsion is used in the emulsion combination and the pH of the resulting nanoemulsion is from 6.5 to 7.5.

As to the nanoemulsion of the present invention (i.e., the solubility of skin benefit agent will be 30 to 500, and preferably, from 75 to 400, and most preferably, from 100 to 350 times greater in the water phase of the nanoemulsion of the present invention than its natural solubility in water at 25° C., atmospheric pressure and neutral pH.

The nanoemulsion of the present invention may be used by a consumer for topical application to the body, especially the hair or skin, most preferably skin. Such a nanoemulsion may be used as an ingredient in an end use composition. When used as an ingredient, the nanoemulsion will typically make up from 5 to 80, and preferably, from 15 to 70, and most preferably, from 20 to 40% by weight of the end use composition, including all ranges subsumed therein. It is also within the scope of this invention for the nanoemulsion with benefit agent to be used as a booster to end use composition (i.e., an enhancer to the benefits provided by the end use composition). Thus, a consumer could obtain a ready to use (end use) composition and supplement the benefits produced by using the same with the nanoemulsion of this invention at the point of use. Therefore, in the case of a cream, for example, the consumer could combine an end use cream with the nanoemulsion of this invention in his or her hands and shear the same prior to or during application to the skin. When used as a booster, the nanoemulsion typically makes up from 2 to 40, and preferably, from 15 to 30% by weight of the resulting composition having a mixture of end use composition and nanoemulsion, whereby the consumer would preferably be instructed to make a homogeneous mixture in his or her hands or when topically applying.

The packaging for the emulsions (including end use compositions) of this invention is typically a bottle, tube or jar. Other suitable packages include blister pack or sachets. The products of the present invention may also be dispensed from automatic dispensers or packaging pressurized with propellant.

The end use compositions suitable for boosting with the nanoemulsions of this invention are limited only to the extent that they may be topically applied to provide a consumer benefit. Superior products made commercially available by Unilever® under the brand names Dove®, Ponds®, Simple®, Vaseline®, Fair and Lovely®, St Ives®, Noxema®, Suave®, Kate Somerville® and the like are especially preferred for use with the nanoemulsions of this invention.

The Examples provided are to facilitate an understanding of the invention. They are not intended to limit the scope of the claims.

Example 1. Nanoemulsion, 1% Cysteine, Oil Continuous and pH 6

High pH (pH 12) macroemulsion and low pH (pH 2.5) macroemulsion were prepared separately. When preparing the high pH macroemulsion (Table 1a), all ingredients in the aqueous phase were combined in a mixing vessel and mixed (at room temperature and with moderate shear) with a magnetic stir bar, resulting in a transparent mixture. The oil phase as prepared by combining and mixing ingredients (also at moderate shear and room temperature) in a separate mixing vessel equipped with an overhead stirrer. Mixing was terminated when the resulting mixture was clear. The aqueous solution was subsequently and gradually added to the mixing vessel with the oil phase while agitation/stirring was provided to mix the two phases. Stirring was stopped after a uniform mixture was obtained and the oil continuous macroemulsion had particle size of about 10 microns.

TABLE 1a

| High pH Macroemulsion | |
|---|---|
| | wt %* |
| Aqueous phase | |
| DI water | Balance |
| NaOH | 0.7 |
| NaCl | 0.4 |
| EDTA | 0.4 |
| Cystine | 1.4 |
| Oil phase | |
| CCT** | 36.6 |
| DC ES-5300*** | 5.8 |

*based on total weight of high pH macroemulsion
**Caprylic Capric Triglyceride
***Silicone Emulsifier, Dow Corning Low pH macroemulsion, about 10 microns, (Table 1b) was prepared in a manner similar to the one described for the high pH macroemulsion described in this example.

TABLE 1b

| Low pH Macroemulsion | |
|---|---|
| | wt %* |
| Aqueous phase | |
| DI water | Balance |
| Citric acid | 2.9 |
| Oil phase | |
| CCT** | 37.1 |
| DC ES-5300*** | 5.8 |

*based on total weight of low pH macroemulsion
**Caprylic Capric Triglyceride
***Silicone Emulsifier, Dow Corning The resulting high pH and low pH macroemulsions were blended in a ratio of 2.6/1, respectively for 2 minutes in a one liter ESCO mixer equipped with a scraper and rotor/stator high shear device (ESCO-LABOR AG, Switzerland), with only the scraper on at a speed of around 50 to 100 RPM. Produced was a mixture having both high and low pH macroemulsions.

Subsequent to making the high and low pH macroemulsion mixture and in the same ESCO mixer, the rotor/stator was activated to shear the mixture at a speed of 3000-6000 rpm for up to 5 minutes and until a nanoemulsion with the droplet size (250 nm) was formed (Table 1c) with 1% by weight cysteine.

TABLE 1c

| Nanoemulsion with 1% cystine | |
|---|---|
| | wt %* |
| Aqueous phase | |
| DI water | Balance |
| NaOH | 0.5 |
| NaCl | 0.3 |
| EDTA | 0.3 |
| Cystine | 1.0 |
| Citric acid | 0.8 |
| Oil phase | |
| CCT** | 36.7 |
| DC ES-5300*** | 5.8 |

*based on total weight of nanoemulsion (particle size 100 nm)
**Caprylic Capric Triglyceride
***Silicone Emulsifier, Dow Corning The results show that making nanoemulsion consistent with this invention unexpectedly results in a nanoemulsion with skin benefit agent (1% by weight) in its aqueous phase.

Example 2. Nanoemulsions with 2 and 2.8% by Weight Cysteine, Oil Continuous and pH 6

The Samples of Example 2 were prepared in a manner similar to the one described in Example 1.

TABLE 2a

| High pH Macroemulsions | | |
|---|---|---|
| | wt %* Sample 1 | wt %* Sample 2 |
| Aqueous phase | | |
| DI water | 38.3 | 53.0 |
| NaOH | 0.7 | 1.0 |
| NaCl | 0.3 | 0.4 |
| EDTA | 0.3 | 0.4 |
| Cystine | 2.0 | 2.7 |
| Oil phase | | |
| CCT** | 26.4 | 36.6 |
| DC ES-5300*** | 4.2 | 5.8 |

*based on total weight of nanoemulsion
**Caprylic Capric Triglyceride
***Silicone Emulsifier, Dow Corning TABLE 2b

| Low pH Macroemulsions | | |
|---|---|---|
| | wt %* | wt %* |
| Aqueous phase | | |
| DI water | Balance | Balance |
| Citric acid | 0.8 | 2.9 |

TABLE 2b-continued

Low pH Macroemulsions

|  | wt %* | wt %* |
|---|---|---|
| Oil phase | | |
| CCT** | 10.3 | 37.1 |
| DC ES-5300*** | 1.6 | 5.8 |

*based on total weight of nanoemulsion
**Caprylic Capric Triglyceride
***Silicone Emulsifier, Dow Corning The results show that making nanoemulsion consistent with this invention unexpectedly results in a nanoemulsion with skin benefit agent (2 and 2.7% by weight) in the aqueous phases.

The invention claimed is:

1. A method for making an oil continuous nanoemulsion comprising the steps of:
   (a) providing, separately, a first and a second oil continuous macroemulsion, the first macroemulsion having a water phase with a pH from 10 to 14 and skin benefit agent in the water phase and the second macroemulsion having a water phase with a pH from 2 to 5;
   (b) mixing the first and second macroemulsions to produce a mixture of macroemulsions, the mixture of oil continuous macroemulsions comprising the water phases with a pH from 10 to 14 and a pH from 2 to 5; and
   (c) shearing the mixture of macroemulsions to produce a nanoemulsion having a water phase, an oil phase and droplets of a particle size from 150 to 900 nm, the nanoemulsion comprising 0.15 to 5% by weight skin benefit agent in the water phase wherein the skin benefit agent is phenylalanine, tyrosine, tryptophan, cystine or a mixture thereof, and wherein a solubility of the skin benefit agent in the water phase of the nanoemulsion is 30 to 500 times greater than its natural solubility in water at 25° C., neutral pH and at atmospheric pressure.

2. The method according to claim 1 wherein the skin benefit agent is cystine and the nanoemulsion water phase comprises the cystine.

3. The method according to claim 1 wherein the pH of the water phase of the first macroemulsion is 11 to 12.5 and the pH of the water phase of the second macroemulsion is 2 to 3.

4. The method according to claim 1 wherein the first and second macroemulsions have water droplets with a particle size from 1 to 30 microns and the nanoemulsion has water droplets with a particle size from 275 to 825 nm.

5. The method according to claim 1 wherein the macroemulsions further comprises a pH adjuster selected from the group consisting of triethylamine, NaOH, KOH, $H_2SO_4$, HCL, citric acid and mixtures thereof.

6. A nanoemulsion made by the method of claim 1.

7. The nanoemulsion according to claim 6 wherein the nanoemulsion comprises cystine, where cystine is present in the water phase and makes up from 0.5 to 3.5% by weight of the nanoemulsion.

8. The nanoemulsion according to claim 6 where the nanoemulsion further comprises vitamin B3 and/or vitamin C in the water phase, and a resorcinol, retinyl propionate, retinyl palmitate, retinyl acetate or a mixture thereof in the oil phase.

9. The nanoemulsion according to claim 6 wherein the droplets of the nanoemulsion have a particle size from 250 to 800 nm.

10. The nanoemulsion according to claim 6 wherein the nanoemulsion can be used with an end use composition to boost a benefit provided by the end use composition.

11. The nanoemulsion according to claim 6 wherein the nanoemulsion further comprises omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol or a mixture thereof.

12. The nanoemulsion according to claim 6 wherein the nanoemulsion further comprises 12-hydroxystearic acid, niacinamide or a mixture thereof.

13. The nanoemulsion according to claim 6 wherein the nanoemulsion further comprises 12-hydroxystearic acid.

14. The nanoemulsion according to claim 6 wherein the nanoemulsion further comprises vitamin A, D, E, K or a mixture thereof.

15. The nanoemulsion according to claim 6 wherein the nanoemulsion further comprises a retinoic acid precursor.

16. The nanoemulsion according to claim 6 wherein the nanoemulsion further comprises a retinyl propionate and a resorcinol.

* * * * *